United States Patent
Halsne et al.

(10) Patent No.: US 9,370,462 B2
(45) Date of Patent: Jun. 21, 2016

(54) PEDIATRIC PATIENT-SAFE CPR DEVICE

(75) Inventors: Eric G. Halsne, Seattle, WA (US); Hans Griesser, Bainbridge Island, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 641 days.

(21) Appl. No.: 13/806,351

(22) PCT Filed: Apr. 27, 2011

(86) PCT No.: PCT/IB2011/051854
§ 371 (c)(1),
(2), (4) Date: Dec. 21, 2012

(87) PCT Pub. No.: WO2012/001541
PCT Pub. Date: Jan. 5, 2012

(65) Prior Publication Data
US 2013/0102936 A1    Apr. 25, 2013

Related U.S. Application Data

(60) Provisional application No. 61/359,995, filed on Jun. 30, 2010.

(51) Int. Cl.
*G09B 23/28* (2006.01)
*A61H 31/00* (2006.01)
*A61N 1/04* (2006.01)
*A61N 1/39* (2006.01)

(52) U.S. Cl.
CPC .......... *A61H 31/005* (2013.01); *A61H 31/007* (2013.01); *A61N 1/046* (2013.01); *A61N 1/0492* (2013.01); *A61N 1/39* (2013.01); *A61H 2201/5061* (2013.01); *A61H 2201/5084* (2013.01)

(58) Field of Classification Search
CPC ... A61H 31/00; A61H 31/004; A61H 31/005; A61H 31/007; A61H 31/008; A61H 2201/5058; A61H 2201/5061; A61H 2201/5071; A61H 2201/5079; A61H 2201/5084; A61N 1/046; A61N 1/0492; A61N 1/39
USPC ...................................... 601/41–44; 607/4–6
See application file for complete search history.

(56) References Cited

U.S. PATENT DOCUMENTS

| | | | |
|---|---|---|---|
| 5,496,257 A * | 3/1996 | Kelly ............................... | 601/41 |
| RE40,471 E | 8/2008 | Groenke et al. | |
| 8,600,522 B2 * | 12/2013 | Peterson et al. ............. | 607/142 |
| 2004/0162510 A1 | 8/2004 | Jayne et al. | |
| 2005/0267536 A1 | 12/2005 | Freeman et al. | |
| 2006/0015044 A1 * | 1/2006 | Stavland et al. ................ | 601/41 |
| 2008/0145827 A1 * | 6/2008 | Strand et al. .................. | 434/265 |
| 2008/0146973 A1 | 6/2008 | Lund et al. | |
| 2008/0300517 A1 | 12/2008 | Nysaether | |
| 2011/0301511 A1 * | 12/2011 | Freeman ......................... | 601/41 |
| 2015/0120201 A1 * | 4/2015 | Silver et al. ..................... | 702/19 |

FOREIGN PATENT DOCUMENTS

EP    1997469 A1    12/2008

* cited by examiner

*Primary Examiner* — Steven Douglas

(57) ABSTRACT

A CPR guidance device for placement and use on the chest of an adult patient. The device guides a rescuer in the application of an adult CPR protocol. The device also senses patient characteristics indicative of an infant patient. If the device senses that the patient in an infant, it appropriately warns the rescuer that the device is for adult patient use only.

9 Claims, 6 Drawing Sheets

PRIOR ART

PRIOR ART

PEDIATRIC PATIENT-SAFE CPR DEVICE

BACKGROUND

Devices that guide cardiopulmonary resuscitation (CPR) during a cardiac arrest rescue have been in existence for a number of years. The QCPR meter, manufactured by Laerdal Medical AS, for example, is a puck-like device which is placed on the patient's chest, over which manual CPR compressions are applied. FIG. 1 illustrates an exemplary CPR meter 20 as applied by a rescuer 12 to an adult cardiac arrest patient 14. Additionally shown is an automatic external defibrillator (AED) 10, which senses the patient's cardiac ECG signals via electrodes 16 placed across the patient's chest.

FIG. 1 shows a typical application of the CPR meter 20 over the patient's sternum. Once placed, the rescuer 12 places his hands over the CPR meter and applies CPR compressions to the patient's chest. The CPR meter 20 senses the force and displacement of the compressions via an internal force sensor and accelerometer and then processes the force and displacement signals with an internal processor. The CPR meter 20 then outputs audible and/or visual instructions for guiding the proper rate and depth of CPR compressions during the rescue. Although FIG. 1 shows that the CPR meter 20 is connected to the AED 10 via a cable, the CPR meter may also be a stand-alone device.

The proper rate and depth of CPR compressions differs between adults and infants. Current CPR Guidelines recommend a 1½" to 2" compression displacement for adults at a rate of about 100 compressions per minute. CPR guidelines for infants are less aggressive at about ⅓ to ½ of the depth of chest at a rate of about 60 compressions per minute. It can be seen that unless the CPR guidance device can discriminate between adult and infant patients, there is a risk that a rescuer will be erroneously guided by the CPR device to apply adult therapy to an infant, and thus potentially injure the infant with inappropriately deep and rapid compressions.

FIG. 2 shows a CPR meter 20 that has been applied to an infant patient 18. Because current AED practice is to apply defibrillation electrodes in the anterior-posterior position, it is seen that the CPR meter 20 is placed over the electrode. Use of the CPR meter 20 in this situation can potentially damage the electrode or the CPR meter during rescue. For these reasons, no prior art CPR meter is indicated for use on infant cardiac arrest patients.

Prior art CPR meters rely on user training to ensure that adult CPR protocols are not mistakenly applied to infants. For example, users of the QCPR meter are trained never to apply the meter to an infant. The labeling also warns against such application. Users of AEDs to which the CPR meter is connected may allow use of the AED on infants by inserting a key which changes the AED operation to an infant mode. Neither solution completely eliminates the risk of improper CPR meter use on an infant. What is needed is an improved method of ensuring that a CPR meter is not used on an infant patient.

SUMMARY

The present invention is a method and apparatus by which a CPR meter detects the inappropriate, and potentially injurious, use of an adult CPR rescue protocol on an infant. Various patient parameters, as sensed by the CPR meter and optionally by a connected defibrillator, are processed to determine whether an infant patient is indicated. The invention provides for a supplemental alert under conditions indicative of misapplication to infants.

In one embodiment of the invention, the sensed patient parameters comprise chest compression displacement and compressions force over an initial one or plurality of CPR compressions. Another embodiment incorporates additional patient parameters, such as trans thoracic impedance and calculated chest height to determine whether the patient is an infant. When the parameter(s) indicate misapplication of the CPR meter to an infant, a visual and/or aural alert is issued to the rescuer that the CPR meter is only for use on adult patients only. Alternatively, the alert may warn the rescuer to stop CPR if the patient is an infant.

Another embodiment of the invention is a method and apparatus by which the CPR meter is configured to avoid the issuance of warnings unless absolutely warranted. Recognizing that the vast majority of CPR rescues are for adults, the invention avoids issuance of repeated, distracting warnings unless absolutely necessary.

DETAILED DESCRIPTION OF THE PREFERRED EMBODIMENTS

Figure 1:
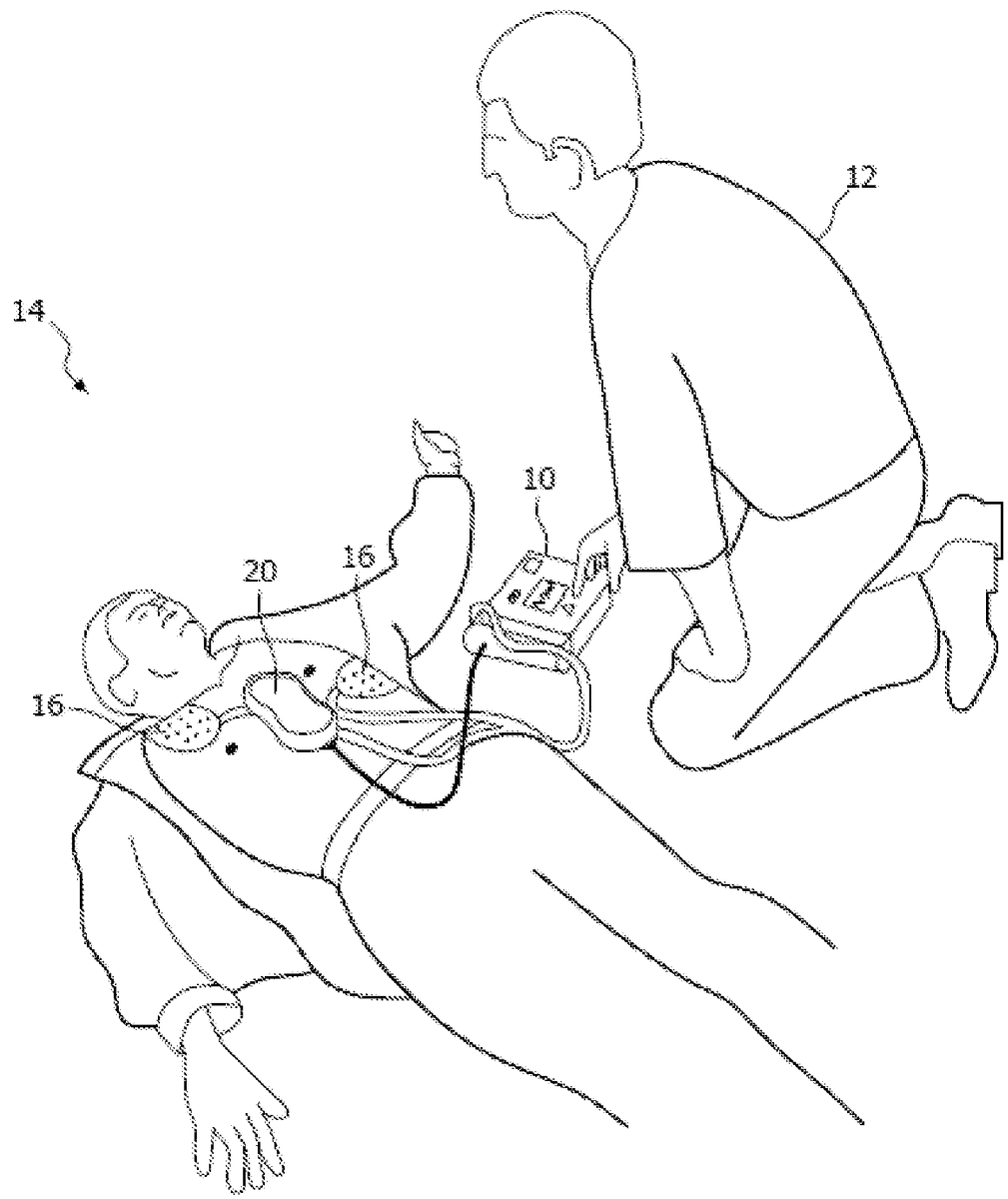
FIG. 1 illustrates a prior art CPR meter as applied to an adult cardiac arrest patient.
Figure 2:
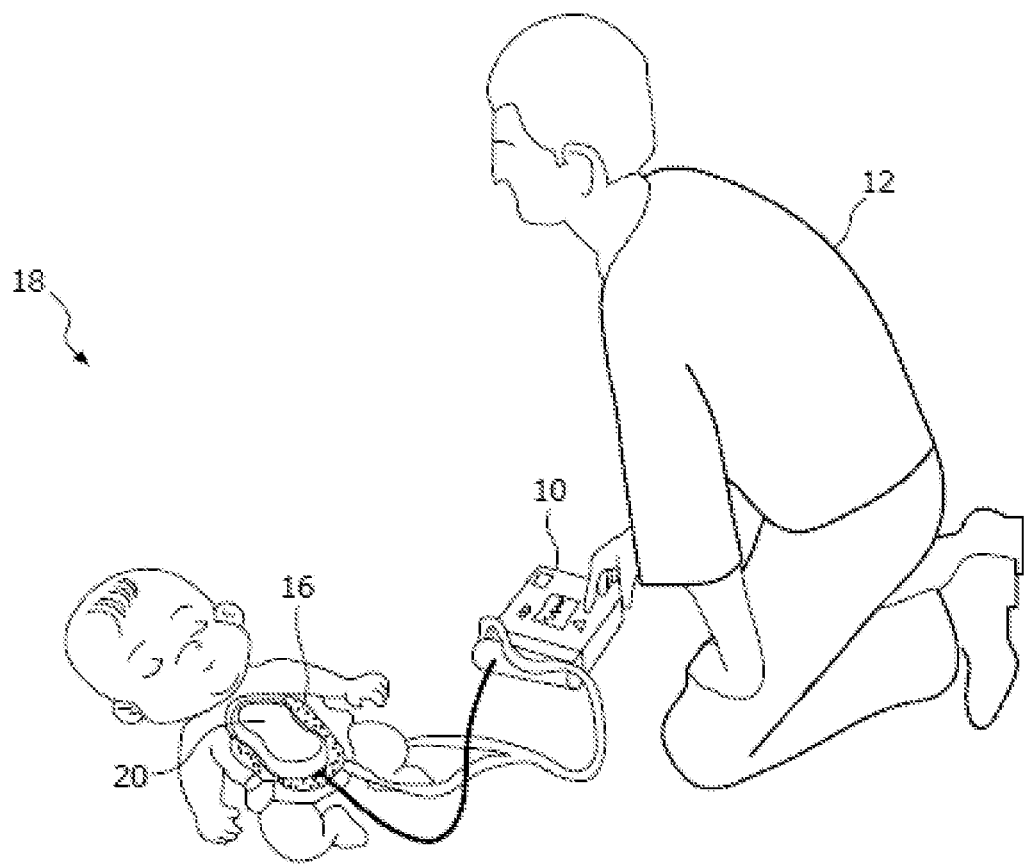
FIG. 2 illustrates a prior art CPR meter as applied to an infant cardiac arrest patient.
Figure 3:
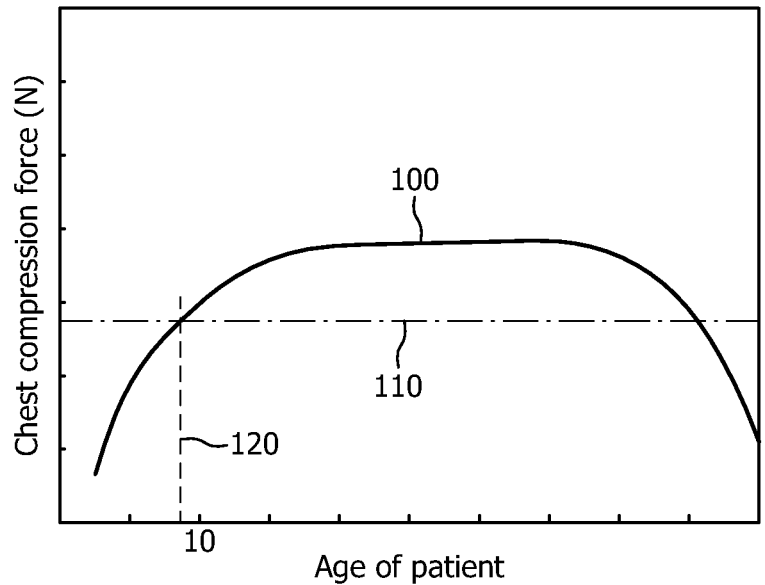
FIG. 3 illustrates a graphical relationship between chest compression force and the patient age.

Turning now to the Figures, several parameters may be used to determine whether the patient is an infant. It should be noted at the outset that no single parameter may be sufficiently accurate to always correspond to infants. For example, experimental evidence suggests that the stiffness of the thorax increases from youth to middle age, and then decreases in the elderly. FIG. 3, showing the trend 100, indicates that a given chest stiffness 110 between elderly patients and infants 120 may be similar. Thus, the chest stiffness parameter alone may not be a sufficiently indicative parameter.

Figure 4:
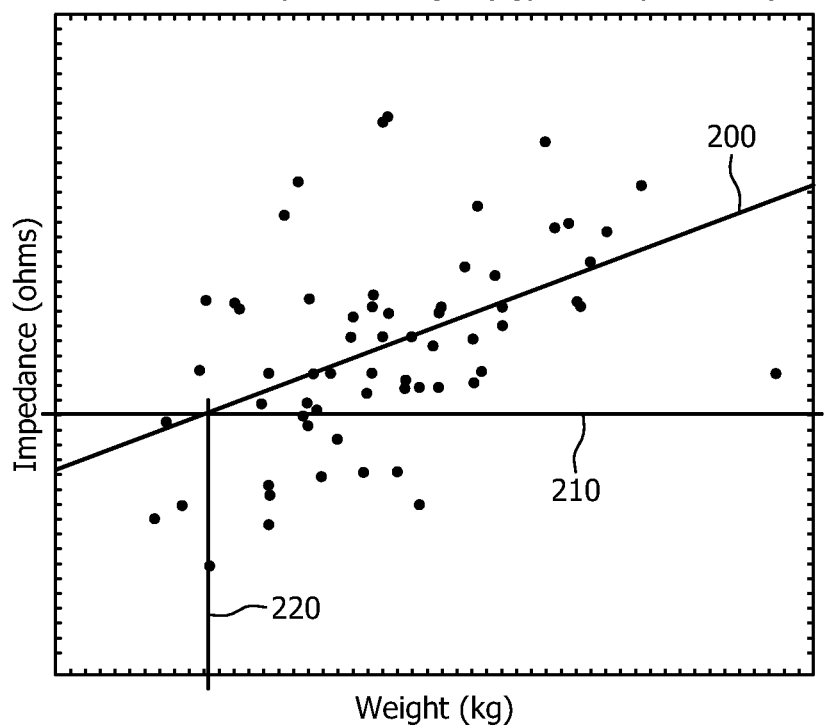
FIG. 4 illustrates a graphical relationship between trans thoracic impedance and the patient weight.

FIG. 4 illustrates another parameter by which trans thoracic (i.e. chest) impedance is correlated to patient weight, and by implication to infant status. As can be seen from the data trend line 200, however, trans thoracic impedance does not correlate well with patient weight. Even though a threshold of weight 220 for infants can be readily established, the threshold impedance 210 will capture a number of false positives (i.e. infant indication in an adult patient).

Figure 5:
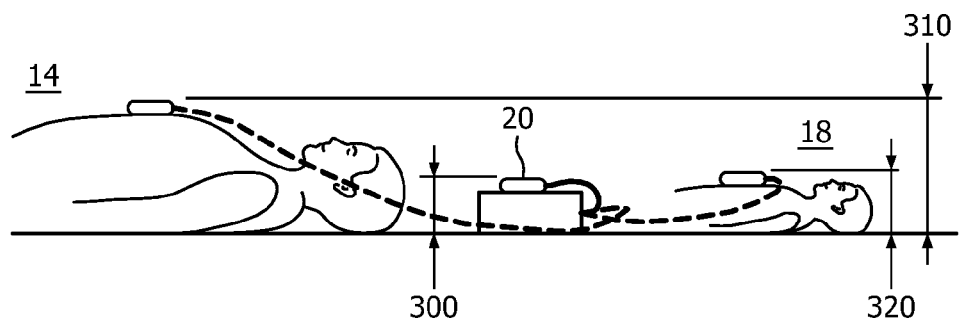
FIG. 5 illustrates relative locational positions for determining the chest wall height of the patient.

FIG. 5 illustrates yet another parameter by which a calculated chest wall height is correlated to infant status. Because infant chest wall heights are smaller than adults, the relative height of the chest wall in a prone patient to a reference surface may indicate infant status. As shown in FIG. 5, this parameter may be measured with the internal accelerometer inside the CPR meter 20 by detecting an initial CPR meter position 300 above a reference surface. The CPR meter position 300 may be ascertained, for example by sensing when the device is activated, when the lid is opened, or by sensing the shock of setting the storage case on the reference surface. The CPR meter may also issue an initial instruction to place the CPR meter on the reference surface. Thus, the CPR meter 20 can "zero" itself at initial position 300.

Subsequent application of the CPR meter 20 to the patient's chest provides another reference point for the accelerometer to determine its cumulative vertical displacement from position 300. An infant chest will be indicated by a small displacement to position 320. An adult chest will be indicated by a greater displacement to position 310. As can be seen, the accuracy of the chest height parameter depends on the proper initial positioning of CPR meter 20 at position 300, which may be unreliable during actual cardiac rescues.

Although an infant determination might be made from any one of the afore-described parameters, a preferred embodiment of the inventive method involves combining several of the parameters in the determination. The selection and relative weighting of the parameters may be accomplished by one of ordinary skill in the art.

Figure 6:
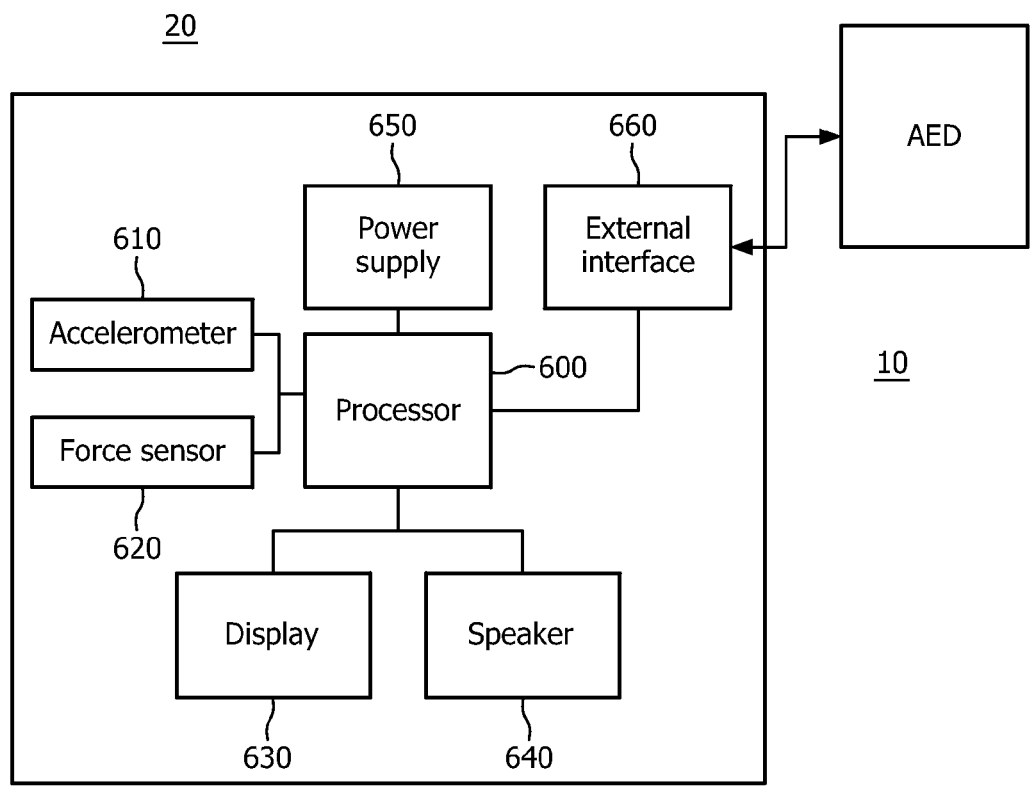
FIG. 6 is a block diagram of a CPR meter according to one embodiment of the inventive apparatus.

FIG. 6 illustrates a block diagram of a preferred embodiment of the CPR meter 20. CPR Meter 20 comprises an accelerometer 610 and a force sensor 620 which sense meter displacement and applied force respectively. A processor 600 receives input from the accelerometer 610 and force sensor 620, using the input in a computer algorithm which determines an indication of whether the meter 20 is being used on an infant. If an infant is indicated, processor 600 controls a visual display 630 to warn the user that an infant is indicated. Additionally or alternatively, processor 600 controls a speaker 640 to issue an appropriate aural warning. Warnings may be, but are not limited to, a warning that the CPR meter is for adult use only, not to use the CPR meter on an infant, or "Stop. An infant use is indicated."

External interface 660 optionally connects the CPR meter 20 with an AED 10. External interface 660 enables parameters of patient trans thoracic impedance obtained from the AED 10 electrodes 16 to be communicated to processor 600. Processor 600 may then use the impedance data as additional information for infant determination. Communication from the processor 600 to the AED 10 can also be provided by external interface 660 so that AED 10 can itself display and issue aural warnings. The link between external interface 660 and AED 10 may be a cable or a wireless link known in the art. Power supply 650, preferably a battery, supplies power to each internal component.

Another exemplary embodiment of a CPR meter 20 that can be modified by the teaching herein is shown in U.S. Patent Publication 2008/0146973 entitled "System for Providing Feedback on Chest Compression in CPR", by Lund et al and hereby incorporated by reference. Lund et al teaches a CPR meter having force and depth measuring, a processing unit, and various displays.

Figure 7:
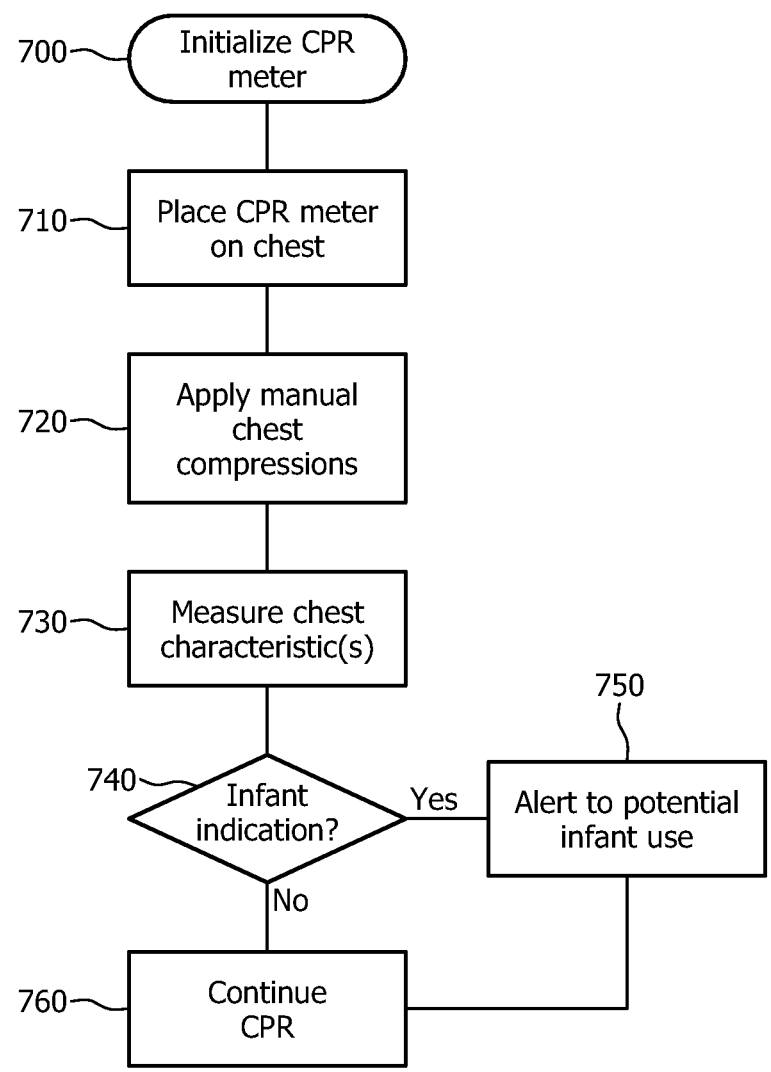
FIG. 7 is a flow chart illustrating one embodiment of the inventive method.

FIG. 7 illustrates a method for preventing a rescuer from performing an adult CPR protocol on an infant human. CPR meter 20 is activated and initialized in step 700. In this step, the CPR meter 20 activates its internal sensors, processors, audible and visual display, and communications paths, as necessary, to ready the device for use. At the completion of step 700, the rescuer prepares the patient for CPR by placing the patient in a prone face-up position, and by exposing and preparing the patient's chest for compressions. In step 710, the rescuer places the activated CPR meter 20 on the patient's sternum, and begins to apply manual compressions over the CPR meter 20 in step 720. The CPR meter 20 senses the beginning of compressions via its internal accelerometer 610 and force sensor 620.

In step 730, the processor 600 within the CPR meter 20 processes the initial compression data to determine the probability that the patient is an infant. If the probability exceeds a threshold and thereby indicates "infant", step 740, an aural and/or visual alert is generated at step 750. The aural alert is preferably a voice command to the rescuer, such as "CPR meter is for adult use only", or "Do not use on an infant." The aural alert may also be sent to a connected AED and issued through the AED speaker.

The visual display is preferably generated on the CPR Meter 20 adjacent to and within view of the rescuer's hands. The display is preferably an illuminated icon showing an infant inside a struck-through circle. The display 630 may flash to attract attention. A connected AED may also display a concurrent icon.

If infant use is not indicated, the CPR meter 20 continues its normal CPR guidance operations under the adult CPR protocol. Because there is evidence that ongoing CPR compressions reduce chest forces and generally re-shape the adult chest cage, any further determination of infant patient should be discontinued for the remainder of the rescue.

Figure 8:
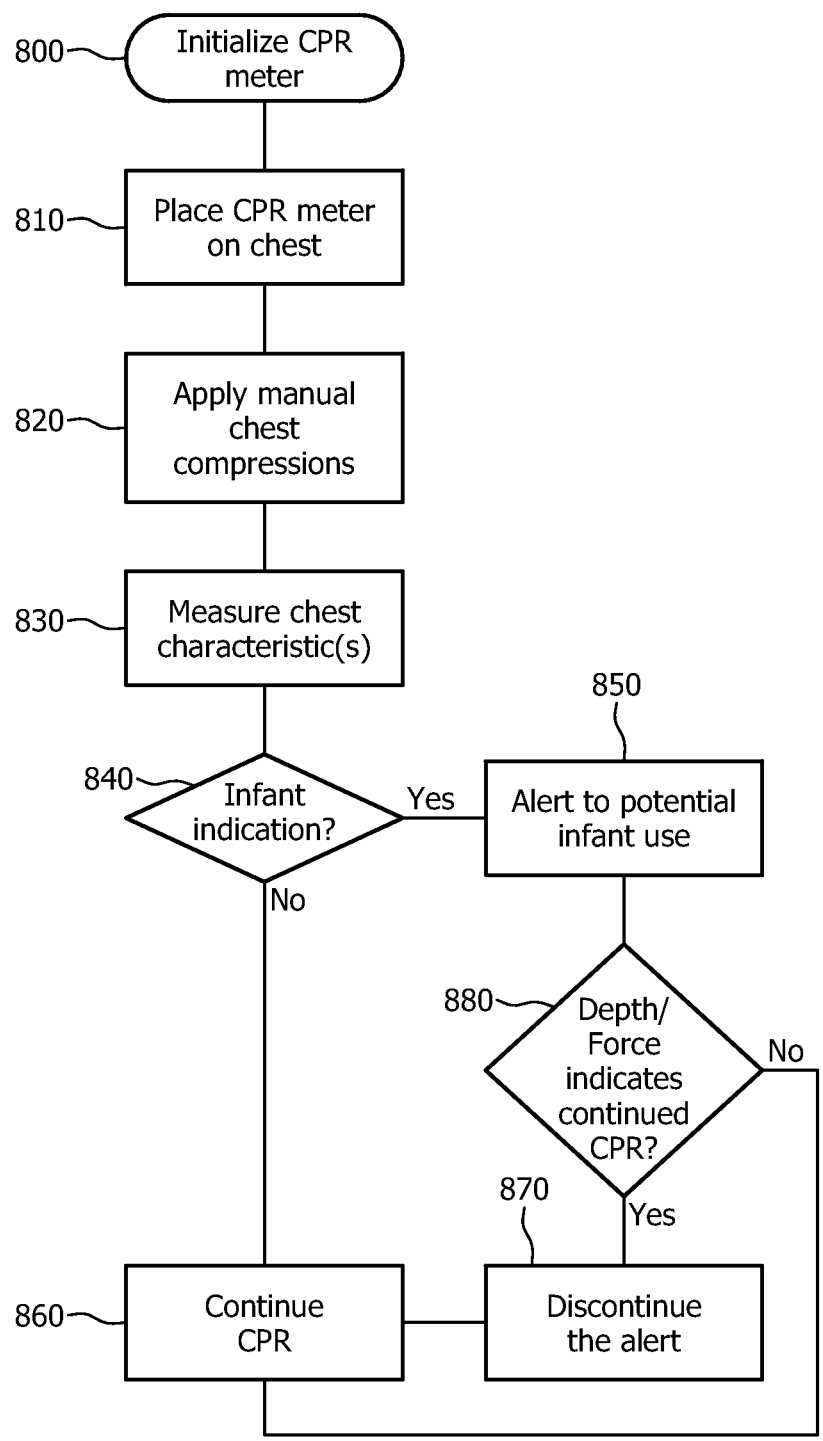
FIG. 8 is a flow chart of yet another embodiment of the inventive method.

FIG. 8 illustrates an alternative embodiment of the method. In the initialization step 800, the CPR meter 20 also determines an indexing height of the CPR meter prior to placement on the patient. Preferably, the indexing height is referenced at a known height above a reference surface, such as the distance between the CPR meter 20 storage case and the floor. An aural instruction to place the CPR meter 20 at a certain location relative to the reference surface may be issued in this step. In step 810, when the CPR meter is placed on the patient's chest, as sensed by an initial applied force and stopping of motion, the processor 600 may use the accelerometer input to determine the total vertical change in height from the reference surface to the top of the chest. If the determined chest height is below a threshold height, the processor 600 may issue an aural or visual alert similar to that previously described in step 750.

In step 830, processor 600 may take additional input from an attached AED via external interface 660 regarding patient impedance values across the AED electrodes. If the patient impedance is below a threshold value, indicating infant application, processor 600 may issue the aural or visual alert in step 850 as previously described in step 750.

If infant use is not indicated, the CPR meter 20 continues its normal CPR guidance operations under the adult CPR protocol, progressing to step 860. At step 860, any further determination of infant patient should be discontinued for the remainder of the rescue.

In the FIG. 8 embodiment, processor 600 continues to analyze the compression depth and force parameters after an alert issues in step 850. If the parameters indicate that CPR is continuing despite the alert, step 880, the alert is assumed to be false. In order to prevent additional distraction and confusion from ongoing false alerting, the alert is then discontinued at step 870.

Returning to step 880, if processor 600 determines that CPR has been discontinued as a result of the alert, the method progresses to step 860. In this case, however, the CPR protocol is adjusted at step 860 to re-orient and get the rescuer back on track. In any event, however, any further determination of infant patient should be discontinued for the remainder of the rescue.

What is claimed is:

1. A method for preventing a rescuer from performing an adult cardiopulmonary respiration (CPR) protocol on an infant human, comprising the steps of:

applying defibrillator electrodes across the chest;

placing a CPR meter to the chest of a human;
manually applying a first set of CPR compressions to the chest with the CPR meter;
measuring a depth of the CPR compressions and a force applied during the CPR compressions;
measuring a trans thoracic impedance across the chest,
determining from the trans thoracic impedance whether the human is an infant; and
alerting the rescuer if the determining step indicates that the human is an infant,
sensing a second set of CPR compressions to the chest with the CPR meter subsequent to the alerting step; and
discontinuing the alerting step based on the sensing step.

2. The method of claim 1, wherein the alerting step comprises an audible indication to the rescuer.

3. The method of claim 2, wherein the audible indication is a voice prompt.

4. The method of claim 1, wherein the alerting step is a visual indication to the rescuer.

5. The method of claim 4, wherein the visual indication is an illuminated icon displayed on the CPR meter.

6. A method for preventing a rescuer from performing an adult cardiopulmonary respiration (CPR) protocol on an infant human, comprising the steps of:
placing a CPR meter to the chest of a human;
establishing an indexing height of the CPR meter prior to the step of placing the CPR meter, wherein the indexing height is referenced at a known height above a reference surface;
sensing the step of placing the CPR meter;
calculating the change in height of the CPR meter between the establishing step and the sensing step;
correlating the change in height to a height of the human chest, and
determining from the height of the human chest whether the human is an infant.

7. A cardiopulmonary resuscitation (CPR) apparatus which is applied to the chest of a human during CPR chest compressions and provides the user guidance in the proper administration of CPR, comprising:
a chest compression depth sensor with a depth signal output;
a chest compression force sensor with a force signal output; and
a processor which determines whether the human is an infant;
a defibrillator operatively connected to the processor,
a plurality of electrodes operatively connected to the processor for sensing a trans thoracic impedance, and
alerting means activated by the processor for alerting the user that the human is an infant,
wherein the processor determines whether the human is an infant based on the trans thoracic impedance,
wherein the processor determines continued CPR compressions from the depth signal output and the force signal output received subsequent to an activated alerting means, and further wherein the processor responsively de-activates the alerting means.

8. The CPR apparatus of claim 7, wherein the alerting means is a speaker.

9. The CPR apparatus of claim 7, wherein the alerting means is a display.

* * * * *